US009402860B2

(12) United States Patent
Kovacs et al.

(10) Patent No.: US 9,402,860 B2
(45) Date of Patent: *Aug. 2, 2016

(54) METHODS OF INHIBITING THE GROWTH OF ONYCHOMYCOSIS AND URUSHIOL-INDUCED ALLERGIC CONTACT DERMATITIS

(75) Inventors: Stephen G. Kovacs, Cary, NC (US); Jerry Chesson, Durham, NC (US)

(73) Assignee: Chesson Laboratory Associates, Inc., Durham, NC (US)

( * ) Notice: Subject to any disclaimer, the term of this patent is extended or adjusted under 35 U.S.C. 154(b) by 1169 days.

This patent is subject to a terminal disclaimer.

(21) Appl. No.: 12/103,353

(22) Filed: Apr. 15, 2008

(65) Prior Publication Data

US 2008/0253984 A1    Oct. 16, 2008

Related U.S. Application Data

(60) Division of application No. 11/284,649, filed on Nov. 22, 2005, now abandoned, which is a continuation-in-part of application No. 10/757,294, filed on Jan. 14, 2004, now Pat. No. 7,008,997, which is a continuation-in-part of application No. 10/223,991, filed on Aug. 20, 2002, now abandoned.

(51) Int. Cl.
| A61K 31/785 | (2006.01) |
| A61K 9/00 | (2006.01) |
| A61K 9/70 | (2006.01) |
| B27K 3/15 | (2006.01) |
| B27K 3/22 | (2006.01) |
| B27K 3/26 | (2006.01) |
| B27K 3/28 | (2006.01) |

(52) U.S. Cl.
CPC .............. *A61K 31/785* (2013.01); *A61K 9/0014* (2013.01); *A61K 9/7015* (2013.01); *B27K 3/15* (2013.01); *B27K 3/22* (2013.01); *B27K 3/26* (2013.01); *B27K 3/28* (2013.01)

(58) Field of Classification Search
CPC .. A61K 31/785; A61K 9/7015; A61K 9/0014
USPC ......... 424/78.02, 78.08, 78.37; 514/482, 862; 528/61, 64, 65, 66, 68, 76, 85
See application file for complete search history.

(56) References Cited

U.S. PATENT DOCUMENTS

| 3,194,793 | A | * | 7/1965 | Kogon | 528/68 |
| 3,438,374 | A | | 4/1969 | Falb et al. | 128/334 |
| 3,892,696 | A | | 7/1975 | Wood | 260/29.2 |
| 4,328,322 | A | | 5/1982 | Baron | 521/163 |
| 4,474,900 | A | | 10/1984 | Dominguez | 521/110 |
| 4,542,012 | A | | 9/1985 | Dell | 424/28 |
| 4,560,555 | A | | 12/1985 | Snider | 424/78 |
| 4,581,432 | A | | 4/1986 | Blum et al. | 528/45 |
| 4,584,192 | A | | 4/1986 | Dell et al. | 424/81 |
| 4,652,493 | A | | 3/1987 | Reichmann et al. | 428/423.1 |
| 4,655,210 | A | | 4/1987 | Edenbaum et al. | 128/156 |
| 4,720,535 | A | | 1/1988 | Schleier et al. | 528/59 |
| 4,733,659 | A | | 3/1988 | Edenbaum et al. | 128/156 |
| 4,806,615 | A | | 2/1989 | Rice et al. | 528/68 |
| 4,913,897 | A | | 4/1990 | Chvapil et al. | 424/59 |
| 4,960,620 | A | | 10/1990 | House et al. | 427/385 |
| 5,013,813 | A | | 5/1991 | Zimmerman et al. | 528/60 |
| 5,039,775 | A | | 8/1991 | Oyaizu | 528/68 |
| 5,091,497 | A | | 2/1992 | Grogler et al. | 528/76 |
| 5,104,930 | A | | 4/1992 | Rinde et al. | 524/871 |
| 5,160,328 | A | | 11/1992 | Cartmell et al. | 604/307 |
| 5,192,536 | A | | 3/1993 | Huprich | 424/78.08 |
| 5,319,058 | A | | 6/1994 | Hattori et al. | 528/67 |
| 5,346,692 | A | | 9/1994 | Wohlrab et al. | 424/61 |
| 5,374,704 | A | | 12/1994 | Muller et al. | 528/66 |
| 5,445,597 | A | | 8/1995 | Clark et al. | 602/48 |
| 5,616,677 | A | | 4/1997 | Primeaux et al. | 528/66 |
| 5,738,627 | A | | 4/1998 | Kovacs et al. | 600/16 |
| 5,763,734 | A | | 6/1998 | Nachtman et al. | 588/1 |
| 5,908,378 | A | | 6/1999 | Kovacs et al. | 600/16 |
| 6,358,503 | B1 | | 3/2002 | Gerrish | 424/78.03 |
| 6,359,100 | B1 | | 3/2002 | Hostettler et al. | 528/58 |
| 6,403,063 | B1 | | 6/2002 | Sawyer | 424/61 |
| 6,495,119 | B1 | | 12/2002 | Sturla et al. | 424/45 |
| 6,531,126 | B2 | | 3/2003 | Farmer | |
| 6,552,155 | B1 | | 4/2003 | Gutman et al. | 528/68 |
| 6,585,967 | B2 | | 7/2003 | Narang et al. | 424/78.31 |
| 6,602,496 | B2 | | 8/2003 | Hedgpeth et al. | 424/78.07 |
| 6,627,216 | B2 | | 9/2003 | Brandt et al. | 424/443 |
| 6,746,667 | B2 | | 6/2004 | Badejo et al. | 424/78.31 |

(Continued)

FOREIGN PATENT DOCUMENTS

| CA | 2 247 906 | 9/1997 |
| EP | 0 114 581 | 8/1984 |

(Continued)

OTHER PUBLICATIONS

MSDS for Desmophen NH 1420.
MSDS for Jeffamine D-2000.
Msds for Poly-A 27-2000.
MSDS for Unilink 4200.
MSDS for Versalink* P-1000 Oligomeric Diamine.
MSDS for Rubinate 9259.
MSDS for Rubinate 9236.
MSDS for Isonate* 143L Modified MDI.
MSDS for Lupranate 81 Isocyanate.
MSDS for Desmodur N 3200.
MSDS for No. 218 Isocyanate.
Ubaghs et al., Novel intermolecular blocked isocynates as stable one-component systems for poly(urea urethane)s, Polymer 46 (2005) 1459-1465.
Lai et al, "A Cross Self-Curing System for an Aqueous-based PU Hybrid", Journal of Applied Polymer Science, vol. 97, 550-558 (2005).
Elchueva et al., "Synthesis of Single-Component Urethane Sealants", Russian Journal of Applied Chemistry, vol. 74, No. 5, 2001 pp. 860-863, Translated from Zharnal Prikladnoi Khimil, vol. 74, No. 5, 2001, pp. 833-837.

(Continued)

*Primary Examiner* — Rabon Sergent
(74) *Attorney, Agent, or Firm* — Myers Bigel & Sibley, P.A.

(57) ABSTRACT

A method for treating onychomycosis and skin conditions such as urushiol-induced allergic contact dermatitis comprises coating the affected nail or skin with a solution comprising an at least a primary diamine with modified diphenylmethane diisocyanates and a carrier solvent/reactant.

16 Claims, 1 Drawing Sheet

(56) References Cited

U.S. PATENT DOCUMENTS

| | | | |
|---|---|---|---|
| 6,784,273 B1 | 8/2004 | Spaans et al. | 528/65 |
| 6,833,408 B2 | 12/2004 | Sehl et al. | 525/54.1 |
| 6,958,154 B2 | 10/2005 | Brandt et al. | 424/400 |
| 7,008,997 B2 * | 3/2006 | Kovacs | 524/770 |
| 7,078,475 B2 | 7/2006 | Klein et al. | 528/64 |
| 8,771,725 B2 * | 7/2014 | Chesson | A61K 8/87 424/447 |
| 2001/0051135 A1 | 12/2001 | Sturla et al. | 424/45 |
| 2002/0037310 A1 | 3/2002 | Jonn et al. | 424/448 |
| 2002/0147462 A1 | 10/2002 | Mair et al. | 606/213 |
| 2003/0007826 A1 | 1/2003 | Badejo et al. | 401/209 |
| 2003/0007946 A1 | 1/2003 | Narang et al. | 424/78.35 |
| 2003/0007947 A1 | 1/2003 | Narang | 424/78.35 |
| 2003/0007948 A1 | 1/2003 | Hedgpeth | 424/78.35 |
| 2003/0007949 A1 | 1/2003 | Hedgpeth et al. | 424/78.35 |
| 2003/0008011 A1 | 1/2003 | Mershon | 424/487 |
| 2003/0080151 A1 | 5/2003 | D'Alessio et al. | 222/129 |
| 2003/0180341 A1 | 9/2003 | Gooch et al. | 424/401 |
| 2004/0062733 A1 | 4/2004 | Birnbaum | |
| 2004/0137067 A1 | 7/2004 | Narang et al. | 424/486 |
| 2004/0147649 A1 | 7/2004 | Kovacs | |
| 2004/0223932 A1 | 11/2004 | Hedgpeth et al. | 424/70.11 |
| 2004/0241130 A1 | 12/2004 | Tamareselvy et al. | 424/70.16 |
| 2004/0242770 A1 | 12/2004 | Feldstein et al. | 525/54.3 |
| 2005/0033251 A1 | 2/2005 | Toreki et al. | 604/367 |
| 2005/0073146 A1 | 4/2005 | Daehne | 285/272 |
| 2005/0181977 A1 | 8/2005 | Hunter et al. | 514/2 |
| 2005/0271794 A1 | 12/2005 | DeSimone et al. | 427/2.1 |
| 2006/0173111 A1 | 8/2006 | Karpowicz et al. | 524/430 |
| 2006/0216267 A1 | 9/2006 | Kovacs et al. | 424/78.27 |
| 2007/0041935 A1 | 2/2007 | Salamone et al. | 424/78.27 |
| 2007/0048355 A1 | 3/2007 | Perlman | 424/443 |

FOREIGN PATENT DOCUMENTS

| | | |
|---|---|---|
| EP | 0 230 387 | 7/1987 |
| EP | 0 409 550 | 4/1995 |
| EP | 0 815 760 | 1/1998 |
| EP | 0 572 416 | 6/1998 |
| EP | 0 857 473 | 8/1998 |
| EP | 0 625 914 | 3/2005 |
| EP | 1 581 568 | 7/2006 |
| JP | 2006212426 | 8/2006 |
| WO | 86/05391 | 9/1986 |
| WO | 95/19751 | 7/1995 |
| WO | 98/02189 | 1/1998 |
| WO | 02/22072 | 3/2002 |
| WO | 2004/024779 | 3/2004 |
| WO | 2004/032713 | 4/2004 |
| WO | 2005/092276 | 10/2005 |
| WO | 2006/101955 | 9/2006 |
| WO | 2007/021620 | 2/2007 |
| WO | 2007/021707 | 2/2007 |
| WO | 2007/025293 | 3/2007 |

OTHER PUBLICATIONS

House, et al., "The Versatility of UOP™ and Clearlink™ Diamines in Polyurethane and Polyurea Systems", UTECH Asia 1996 Conference Paper, 16 pages.

Reddinger et al., "Tuning the Properties of Polyurea Elastomer Systems via Raw Material Selection and Processing Parameter Modulation", PU Latin America 2001, Rapra Conference Proceedings 2001, 9 pages.

Scott et al., "The Effect of Unilink 4200 on Spray Polyurea Coatings", UPO LLC, Hunstman Polyurea Training Seminar, Aug. 27, 2001, 24 pages.

Extended European Search Report corresponding to European Application No. 06839991.4 issued Oct. 16, 2012.

First Examination Report corresponding to European Application No. 06839991.4 issued Mar. 25, 2014.

* cited by examiner

POLYTETRAMETHYLENE OXIDE-DI-P-AMINO BENZOATE $r$ = end-to-end distance
$s$ = radius of gyration

METHODS OF INHIBITING THE GROWTH OF ONYCHOMYCOSIS AND URUSHIOL-INDUCED ALLERGIC CONTACT DERMATITIS

This application is a divisional application of U.S. patent application Ser. No. 11/284,649, filed Nov. 22, 2005, now abandoned, which is a Continuation-In-Part of U.S. patent application Ser. No. 10/757,294, which issued as U.S. Pat. No. 7,008,997, which is a Continuation-In Part of U.S. patent application Ser. No. 10/223,991, now abandoned, each of which is incorporated herein by reference in its entirety.

BACKGROUND

This application is a divisional application of U.S. patent application Ser. No. 11/284,649, filed Nov. 22, 2005, which is a Continuation-In-Part of U.S. patent application Ser. No. 10/757,294, which issued as U.S. Pat. No. 7,008,997, which is a Continuation-In-Part of U.S. patent application Ser. No. 10/223,991, each of which is incorporated herein by reference in its entirety.

The present invention relates generally to a system and method of inhibiting the growth of onychomycosis (toe fungus) and skin conditions such as urushiol-induced allergic contact dermatitis (poison ivy, oak and sumac reactions), and in particular to a polymer chemistry device that provides a hydrophobic, elastomeric topical agent for inhibiting the growth of these conditions and for mitigating of the deleterious effects thereof.

Onychomycosis is a fungal infection of the nails commonly known as toe fungus, although it also attacks fingernails. Onychomycosis is caused primarily by dermatophytes, a type of fungi, such as *Trichophyton rubrum* and *Trichophyton mentagrophytes*. Yeasts such as *Candida albicans* cause a small number of cases, usually fingernail infections, and molds such as *Scopulariopsis, Scytalidium, Acremonium*, and *Fusarium* cause additional cases. Dermatophytes grow in the nail bed beneath the nail, and live off keratin, the protein in the nail. The condition usually begins towards the far end of the nail and may start with patches of white or yellow discoloration.

If the condition is left untreated, it will proceed to the base of the nail. It will attack the nail root (matrix) and cause the nail to grow very thick and deformed. The big toe is usually the first nail to be affected with the condition spreading to adjacent nails. In rare cases this condition can also affect the skin surrounding the nails. Debris may collect under the nail, causing a foul smell. The nail may thicken and become flaky. Thick toenails, in particular, may cause discomfort in shoes and may even make standing and walking painful for the affected individual. Onychomycosis of the fingernails may restrict typing, writing, and computer work; dressing; manual dexterity, fine touch, and sensitivity; and social interaction.

There are four types of onychomycosis. Distal and/or lateral subungual onychomycosis affects the nail bed and nail plate. Proximal subungual onychomycosis affects the proximal nail fold, with infection extending distally under the nail plate. Superficial white onychomycosis affects the top of the nail plate. Candidal onychomycosis affects the nail, skin, and mucous membranes.

Onychomycosis is often treated with terbinafine, an oral or topical antifungal agent (brand name: Lamisil®). Terbinafine is attracted to keratin, the food source of dermatophytes. Terbinafine acts by interfering with the ability of fungi to make sterols, which are an important part of the membrane that surrounds fungal cells and holds them together. Depriving the fungi of sterols weakens the cell membrane. Terbinafine is prescription medication. Topical terbinafine was approved by the FDA in 1993, and terbinafine oral tablets were approved in 1996. Other antifungal agents used the treatment of onychomycosis are griseofulvin (Fulvicine®; Gris-Peg®) and itraconazole (Sporanox®).

While medications for treating onychomycosis are readily available, they are prescription drugs that must be dispensed by a licensed medical professional. This usually requires that an individual suffering from onychomycosis be examined by a doctor, an expense many people cannot afford. Additionally, the prescription drugs themselves are expensive, and must be taken according to a dosing regimen, often for several months.

Poison ivy, oak, and sumac belong to a family of plants that produce urushiol, an oil that causes one of the most common allergic reactions in the United States. Experts estimate that up to 70% of the U.S. population is allergic to urushiol. The American Academy of Dermatology estimates that there are up to 50 million cases of urushiol-induced dermatitis annually in the United States alone. It accounts for 10% of all lost-time injuries in the United States Forest Service.

The allergen urushiol attaches to the skin within five minutes to two hours after exposure, most commonly by physical contact with the leaves or sap of plants such as poison ivy (*Toxicodendron radicans* or *Rhus toxicodendron*), poison oak (*Toxicodendron diversilobum* or *Rhus diversiloba*), or poison sumac (*Toxicodendron vernix* or *Rhus vernix*). Chemically, urushiol is harmless to humans. However, it binds to skin cell membranes and initiates a T-cell mediated immune response. That is, urushiol changes the configuration of skin cell membranes, so that the body's immune system no longer recognizes these cells as belonging to the body and attacks them as foreign. The result is an allergic eczematous contact dermatitis characterized by redness, swelling, papules, vesicles, bullac, and streaking. The dermatitis causes itching, and excessive scratching may lead to infection.

Zanfel® and Tecnu® are commercial preparations that remove urushiol from the skin, if applied immediately following exposure. However, they are less effective once an outbreak has occurred. Calamine lotion, antihistamines, and hydrocortisone ointment are over-the-counter treatments commonly used to abate the symptoms of urushiol-induced allergic contact dermatitis once an outbreak develops. A dermatologist may prescribe a course of corticosteroids to neutralize the itch. Commonly prescribed drugs are prednisone and betamethasone dipropionate (Diprolene®). These drugs require the inconvenience and expense of an examination and prescription by a dermatologist. A variety of home remedies are known (or alleged); most are ineffective.

A need exists in the art for an inexpensive, non-prescription, safe, easily applied device that inhibits the growth of onychomycosis and urushiol-induced allergic contact dermatitis, and that alleviates or at least mitigates the deleterious effects of these conditions.

SUMMARY OF THE INVENTION

As described in one or more parent applications, the present inventors developed various non-toxic, non-carcinogenic, hydrophobic, elastomeric, polymer-based chemistry formulations for wood preservation, as an alternative to the common practice of treating wood using heavy metals and environmentally hazardous ingredients. The inventors have made the surprising discovery that these chemistry formulations have efficacy as topical treatments for conditions such as onychomycosis and urushiol-induced allergic contact dermatitis.

In one embodiment of the present invention there is provided a method for treating onychomycosis or urushiol-induced allergic contact dermatitis by making a polymerizable, elastomeric, hydrophobic thermoset material, by combining at least a primary diamine with modified diphenylmethane diisocyanates and one or more carrier solvent/reactant(s) to form a solution; topically applying the solution to toe nail or fingernail infected with onychomycosis or skin experiencing an outbreak of urushiol-induced allergic contact dermatitis; and drying the solution to form a polyureathane linked copolymer coating that inhibits growth of the onychomycosis or urushiol-induced allergic contact dermatitis, and/or mitigates the deleterious effects thereof. In one embodiment, the primary diamine may be mixed with a secondary diamines in an oligomeric, stoichiometrically balanced blend.

In another embodiment, a composition for the topical treatment of onychomycosis and urushiol-induced allergic contact dermatitis comprises a mixture of a primary diamine in a volume ratio ranging from about 3.6% to about 12.2% v/v of the total solution; a chain extension reagent in a volume ratio ranging from about 2.0% to about 6.2% v/v of the composition; and a stabilizing carrier in an amount sufficient to prevent formation of a gel or solid prior to removal of a portion of the stabilizing carrier.

DETAILED DESCRIPTION OF THE INVENTION

Figure 1:
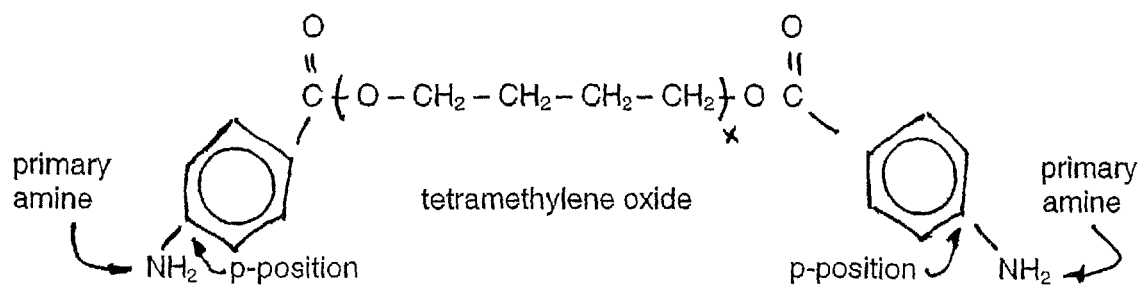
FIG. 1 is a chemical diagram of polytetramethylene oxide-di-p-amino benzoate.

The formulations for topical treatments for onychomycosis and urishiol-induced allergic contact dennatitis are essentially developed as a single, sequential step mixing process wherein the desirable properties of the formulations are obtained by blending the desired reactants in a single sequential step procedure. For example, the following blend/mixture of components has been determined effective in treating onychomycosis or urushiol-induced allergic contact dermatitis:

1) A primary diamine, or an oligomeric, stoichiometrically balanced blend of primary and secondary diamines, as a pre-polymer.

2) Specific modified diphenylmethane diisocyanates used for polymer chain extension in order to obtain a cured polyireathane/urea polymer.

3) A primary carrier solvent/reactant, such as for example acetone aka propanone.

4) Optionally, a secondary carrier solvent/reactant, such as for example mineral spirits.

5) Optionally, additives, such as a polyether oxyalkylene polyol to reactively support the carrier solvent/reactant(s), and/or an amine-functional reactive partner (resin) to crosslink with aliphatic polyisocyanates for polymer chain extension.

These components, in stoichiometrically balanced volume ratios, provide treatment devices with a range of material characteristics ably suited for various application requirements. The sequential mixing process is normally done at ambient conditions of 70-80 Fahrenheit, about 750-760 mm Hg, and relative humidity of 50-65%.

The mixture of these components to obtain a urea-linked polyureathane co-polymer is governed by the well-principled science of stoichiometric chemistry. Stoichiometric chemistry mix requirements for compatible polymeter components of various average molecular weight and various NCO % content are well known and practiced by those skilled in the science of polymer chemistry.

Suitable materials for each of these classifications are discussed below, followed by a description of the suspected mechanics underlying the delayed polymerization exhibited by the present invention. Following a discussion of the mechanics of the present invention as a device for treating onychomycosis and skin conditions such as urushiol-induced allergic contact dermatitis, specific examples of commercially available suitable components are listed, as are examples detailing actual experimental results.

Diamines

In one or more embodiments, an oligomeric blend of diamines developed for the present invention consists of a primary diamine and a secondary diamine. In other embodiments, a single diamine is used. The amine functionality is capped onto the ends of the soft segment. Chain extension, or polymerization, is accomplished by using MDI, modified forms of monomeric MDI, or MDI containing resins as the hard segments. Elastomers prepared from such generic formulations exhibit the best overall physical properties of liquid-phase cast elastomers, although other soft segments can be used—polyether, polyester, polycarbonate, or polypropylene glycol. TDI-amine elastomers contain urethane and urea linkages, while MDI-polyol elastomers contain only urethane linkages. MDI-amine elastomers contain only polyureathane/urea linkages.

Isocyanates

A suitable polyisocyanate for use in the polymer chemistry system of the present invention is one that is conventionally employed in the production of polyurethanes.

Examples of monomeric polyisocyanates useful herein include polyisocyanates and polyisothiocyanates which are PAPI-1 (a polyaryl polyisocyanate as defined in U.S. Pat. No. 2,683,730), tolylene diisocyanate "TDI", triphenylmethane-4,4'4"-triisocyanate, benzene-1,3,5-triisocyanate, toluene-2,4,6-triisocyanate, diphenyl-2,4,4'-triisocyanate, hexamethylene diisocyanate, xylylene diisocyanate, chlorophenylene diisocyanate, diphenylmethane-4,4'-diisocyanate, naphthalene-1,5-diisocyanate, xylene-alpha, alpha'-diisothiocyanate, 3,3'-dimethyl-4,4'biphenylene diisocyanate, 3-3'dimethoxy-4,4'-biphenylene diisocyanate, 2', 3,3'-dimethyl-4, 4'-biphenylene diisocyanate, 5,5'-tetramethyl-4,4'biphenylene diisocyanate, 2,2', 5,5'-tetramethyl-4,4'biphenylene diisocyanate, 4,4'methylenebis(phenylisocyanate), 4,4'-sulfonylbis (phenylisocyanate), 4,4'-methylene di-orthototylisocy anate, ethylene diisocyanate, ethylene diisothiocyanate, trimethylenediisocyanate and the like. Mixtures of any one or more of the above mentioned organic isothiocyanates or isocyanates may be used as desired.

Additionally suitable are mixtures of TDI such as a mixture (80/20 by weight) of 2.4-toluene diisocyanate and 2,6 toluene diisocyanate or a mixture (65/35 by weight) of 2,4-toluene diusocyanate and 2,6-toluene diisocyanate; tetramethylene diisocyanate; hexamethylene diisocyanate; xylene diisocyanate; 1,5-napththylene diisocyanate; 1,4-phenylene diisocyanate; 4,4'-diphenylmethane diisocyanate (MDI) (Upjohn's ISONATE® 125M); 4,4'4"-triphenylmethane triisocyanate; and 3,3'-dimethyl-4.4'-diphenylmethane diisocyanate. Aliphatic diisocyanates such as the $C_{36}$ aliphatic diisocyanate derived from the dimer of ricinoleic acid can be suitably employed and are commercially available, for example, as DDI-1410 (Henkel Corporation, Resin Division, Minneapolis. Minn.). The polyisocyanates hereof are known polyisocyanates in the field of polyurethane technology and can be employed singly or in admixture. Other examples of such polyisocyanates can be found, for example, in *The Development and Use of Polyurethane Products*, E. N. Doyle, McGraw-Hill Book Company, page 27 (1971) and *Polyurethane Handbook*, Gunter Oertel Hauser. Gardner Press (1994).

Preferred polyisocyanates for employment in the process of the present invention are polyisocyanate materials in a liquid form at ambient temperatures, e.g., a liquid MDI product as disclosed in U.S. Pat. No. 3,394,164. These materials facilitate the production of polymeric products from normally liquid oligomeric aminobenzoic acid esters or amides and obviate the requirement of melting a solid polyisocyanate as a prerequisite to providing a suitable reaction mixture. Suitable liquid polyisocyanate materials are known and include, for example, polymeric MDI (4,4'-diphenylmethane diisocyanate) products obtained as by-products from the synthesis of MDI.

In the production of MDI by the condensation of aniline with formaldehyde and the conversion of amino to corresponding isocyanate groups, a content of the initially formed bis-adduct of aniline and formaldehyde reacts further with the reaction mixture to form polymeric aniline derivatives which are in turn converted to isocyanates. Typically, such polymeric derivatives will have a functionality of from about 4 to about 15, for example, about 10 isocyanate groups per molecule. Products containing such polymeric polyiscocyanates in the form of a pot residue after removal of pure MDI by distillation can be utilized. Similarly, polyisocyanate products comprising such polymeric polyisocyanate species in admixture with pure MDI, i.e., the undistilled reaction mixture, can be employed. Polymeric MDI products can be employed herein to advantage and are commercially available under such trade designations as RURBINATE® M, RURBINATE® LF-168 and RURBINATE® LF-209 (available from Rubicon Chemicals Inc. Geisman. La.) and PaPI 27, PaPI 135, PaPI 580 and PaPI 901 (available from the Upjohn Company, Kalamazoo, Mich.).

Another liquid polyisocyanate material which can be employed where crosslinking is desirably introduced into the polymeric products hereof comprises an admixture of MDI and a tri-functional cycloaddition product of MDI. An admixture of MDI and a trifunctional cycloadduct having the following structure, where R is

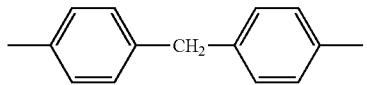

can be employed:

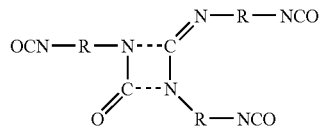

Such an admixture is available under the designation "Liquid MDI, Isonate 143L" (The Upjohn Company, Kalamazoo, Mich.).

To reiterate, in addition to the preferred MDI, modified forms of monomeric MDI or MDI-containing resins, any suitable organic diisocyanate may be used in the process of this invention such as, for example, aliphatic diisocyanates, aromatic diisocyanates, alicyclic diisocyanates, and heterocyclic diisocyanates including such as, for example, ethylene diisocyanate, ethylidene diisocyanate, propylene diisocyanate, butylene diisocyanate. cyclopentylene-1,3-diisocyanate, cyclohexylene-1,4-diisocyanate,cyclohexylene-1,2.diisocyanate, 2,4-tolylene diisocyanate, 2,6-tolylene diisocyanate, 4,4'-diphenylmethane diisocyanate, 2,2-diphenylpropane-4, 4'-diisocyanate, p-phenylene diisocyanate, m-phenylene diisocyanate, xylylene diisocyanate, 1,4-napthylene diisocyanate, 1,5-naphthylene diisocyanate, diphenyl-4,4'diisocyanate, azobenzene-4,4'-diisocyanate, diphenylsulfone-4,4'-diisocyanate, dichlorohexamethylene diisocyanate, tetramethylene diisocyanate, pentametylene diisocyanate, hexamethylene diisocyanate, 1-chlorobenzene-2,4-diisocyanate, furfurylidene diisocyanate, triphenyl methane triisocyanate and the like.

Other examples of suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-and-1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)-methane, 2,4'dicyclohexyl-methane diisocyanate, 1,3- and 1,4-bis(isocyanatomethyl)-cyclohexane, bis-(4-isocyanato-3-methyl-cyclohexyl)-methane, α, α, α', α'-tetramethyl-1,3-1-isocyanato-1-methyl-4-(3)-isocyanatomethyl cyclohexane, 2,4-, 1,3- and/or 1,4-phenylene diisocyanate, 2,4- and/or 2,6-toluylene diisocyanate, 2,4- and/or 4,4'-diphenyl-methane diisocyanate, 1,5-diisocyanato naphthalene and mixtures thereof. Aromatic polyisocyanates containing 3 or more isocyanate groups such as 4,4',4"-triphenylmethane diusocyanate.

In accordance with the present invention, the polyisocyanate component can be in the form of an NCO prepolymer or a polyisocyanate adduct, more preferably a polyisocyanate adduct. Suitable polyisocyanate adducts are those containing, isocyanurate, uretidone, biuret, urethane, allophanate, carbodiimide and/or oxadiazinetrione groups. The polyisocyanates adducts have an average functionality of 2 to 6 and an NCO content of 5 to 30% by weight. The isocyanato-isocyanurateg generally have an average NCO functionality of 3 to 3.5 and an NCO content of 5 to 30%, preferably 10 to 25% and most preferably 15 to 25% by weight.

Preferred polyisocyanate adducts are the polyisocyanates containing isocyanurate groups, biuret groups or mixtures of isocyanurate and allophanate groups.

The NCO prepolymers, which may also be used as the polyisocyanate component in accordance with the present invention, are prepared from the previously described monomeric polyisocyanates or polyisocyanate adducts, preferably monomeric diisocyanates, and organic compounds containing at least two isocyanate-reactive groups, preferably at least two hydroxy groups. These organic compounds include high molecular weight compounds having molecular weights of 400 to about 6,000, preferably 800 to about 3,000, and optionally low molecular weight compounds with molecular weights below 400. The molecular weights are number average molecular weights (Mn) and are determined by end group analysis (OH number).

With regard to the organic diisocyanates, the prepolymers and the polyisocyanate adducts, reference is made to U.S. Pat. No. 5,516,873, which is incorporated by reference hereinto in its entirety.

Carrier Solvent/Reactants

A suitable stabilizing carrier is one which will completely dissolve the selected aromatic diamine derivative and the selected polyisocyanate when they are combined to form a reaction solution but which will prevent the resultant polymeric reaction product, i.e. the polyurea, from solidifying or gelling out of the reaction solution. In other words, the stabilizing carrier either prevents the normally near instantaneous reaction between the isocyanate group and the amino group or prevents the resultant reaction product, e.g., polyurea, from solidifying or gelling until such time as a portion of the stabilizing carrier or solvent is removed from the resultant solution, e.g., as by evaporation.

A suitable stabilizing carrier comprises a stabilizing solvent selected from:
an aldehyde or ketone of the formula

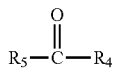

where $R_4$ and $R_5$ are independently of each other hydrogen and lower alkyl or $R_4$ and $R_5$ are joined to form a five or six membered ring; where the term "lower" is as previously defined; and where the term "alkyl" is as previously defined;
(b) an ester having the formula

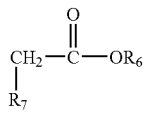

where $R_6$ and $R_7$ are loweralkyl (as previously defined) and $R_7$ additionally is H and loweralkoxy where the term "lower" is as previously defined and the term "alkoxy" is as previously defined;
(c) ortho, meta- or para-dimethylbenzene;
(d) N-methylpyrrolidone;
(e) Solvesso solvent;
(f) a petroleum hydrocarbon;
(g) a lactone of the formula

(loweralkylene) where "lower" and "alkylene" is as previously defined; such as γ-butyrolactone; and
a mixture of any of the foregoing solvents; combined with at least one polyol of the formula HO-loweralkylene-OH where "lower" and "alkylene" is as previously defined.

Some suitable aldehydes and ketones, for example, include acetone, methyl ethyl ketone, methylisobutylketone, N-methylcyclohexanone, acetaldehyde, propionaldehyde, butryaldehyde and isobutyraldehyde. Some suitable solvents of formula (b) include methyl acetate, ethyl acetate, butyl acetate, and methoxy propyl acetate. Some suitable polyols include, for example, polyglyols of the formula

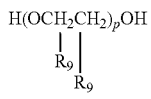

(10)

where p is an integer equal to 1 to 14, as for example when p is equal to 1 to 3, such compounds as ethylene glycol, propylene glycol, butylene glycols, such as 1,3-, 1,4-, and 2-3-butylene glycol, and alkylene glycols having 5 to 9 carbon atoms; when n is 4 or greater, polyglycols of an average molecular weight of about 600, such as polyethylene glycol 200, polyethylene glycol 400 and polyethylene glycol 600. It is to be understood that a mixture of the stabilizing solvents, e.g. aldehydes and ketones, can be employed, as well as a mixture of polyols, e.g., a mixture of ethylene glycol and propylene glycol.

The selected aromatic diamine derivative and the selected polyisocyanate components are added to the stabilizing carrier solution to form a reaction solution. Conventionally, these reaction components are combined in the stabilizing carrier in solution in substantially equivalent proportions, that is in amount of the polyisocyanate of about 0.9 to 1.2 equivalents per equivalent of the first component of oligomeric aromatic diamine derivative, based upon the isocyanate groups and amino groups, respectively, of the polyisocyanate and oligomeric diamine derivative reactants. Typically, from about 1.0 to about 1.15 equivalent of polyisocyanate material per equivalent of the first component e.g., diamine derivative is employed.

Preferably, the primary reactants, e.g. oligometrice diamine derivative, and the polyisocyanate are combined in a volume ratio whereby the isocyanate is in excess to the ester or amide or diamine and is expressed in the following manner:

$$\frac{100}{0.95} \times \frac{1}{\text{Total Equivalent Weight of the first component e.g. the oligomeric primary diamine}} \times \text{the polyisocyanate second component} = \text{percent volume of}$$

which gives the parts of the polyisocyanate per 100 parts of the first reactant e.g. the oligomeric diamine derivatives.

The amount of carrier agent employed is one which is sufficient to dissolve the first reactants e.g. the oligomeric diamine derivatives, and the polyisocyanate second reactant and maintain the reaction product thereof, i.e., the polyurea, in solution without the precipitation out or gelling of the polyurea product. Typically, the amount of stabilizing carrier employed is about 10 to 80% of the total reaction solution volume. Typically the amount of the stabilizing solvent, e.g. aldehyde and/or ketone, employed with at least one polyol is in the ratio of 10 to 80 parts of solvent to one part of polyol. The amount of stabilizing solvent, e.g. acetone, is adjusted depending upon the viscosity desired for specific application requirements, e.g. for maximum penetration and an ultrathin coating thickness for glass, plumbing fixtures, furniture coatings, to a heavy gauge coating thickness for substrates having heavy chemical or environmental corrosion exposure. Typically, the reaction product viscosity will range from about 3.5 centipoise to about 1800 centipoise at room temperature.

The oligomeric diamines in the stabilizing carrier typically react with the polyisocyanate at room temperature; however, the reaction solution can be heated to affect reaction.

The resultant reaction solution is a 'single pot' polyurea composition that can be stored for a long period of time, e.g. 6-9 months at 25° C. without exhibiting any instability or gelling out of the polyurea. Accordingly, this single pot composition can be applied in any manner for a synthetic polymer process, e.g., casting, molding, spraying, etc., where, after application, the single pot composition is treated, e.g. by heating, vacuum evaporation, etc., to remove at least a portion of the stabilizing carrier, leading to the formation of a solid, cured polyurea material.

Additives

While the process and the single pot formulation permits the production of polymeric materials without the use of blocking agents, end-capping chemical modifications or thermally activated catalysts, e.g. caprolactum, B-carbonyl compounds (such as ethyl aceto acetate, ethyl malonate), alcohols and oximes; polymerization additives of various types employed in the manufacture of polymeric products can desirably be employed. For example, such polymerization agents as catalysts, ultraviolet absorbers, fillers, plasticizers, blowing agents, etc., can be employed where desired.

Typically a flow and leveling agent polymerization additive is employed. Preferably such additive comprises a glycidyl-ester of neo decanoic acid, of the formula

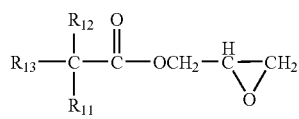

where the $R_{10}$, $R_{11}$, $R_{12}$ are independently of each other H and lower alkyl where the sum of each alkyl group of $R_{10}$, $R_{11}$, and $R_{12}$ does not exceed 8 carbon atoms.

Other flow and leveling agents include the diglycidyl either of 1.4-butane diol, the diglycidyl ether of neopentyl glycol, the poliglycidyl ether of aliphatic polyols, phenyl glycidyl ether, nonyl phenyl glycidyl ether, $C_9$-$C_{18}$ glycidyl ether of castor oil, trimethyol ethane of triglycidyl ether and the ester forms of the aforementioned ethers. These ethers and esters are commercially available from the Shell Chemical Company and are designated as HELOXY®. The glycidyl neodecanoate is commercially available from Exxon Chemical Company and is known as GLYDEXX N®-10.

Additionally, employed is an ultraviolet (UV) light absorber such as benzotriazoles, e.g. benzotriazoles disclosed in U.S. Pat. Nos. 3,004,896 and 3,189,615. Such benzotriazoles are commercially available from Ciba Geigy as Tinuyin® products, such as Tinuvin® P. (2-(2H-benzotriazol-2yl))-4-methylphenol); Tinuvin® 1130, comprising about fifty-two weight percent of poly {oxy-1,2-ethanediyl), α-(3-(3-(2H-benzotriazol-2-yl)-5-(1,1-dimethylethyl)-4-hydroxypheny-1)-oxopropyl)-ω-hydroxy, of the formula

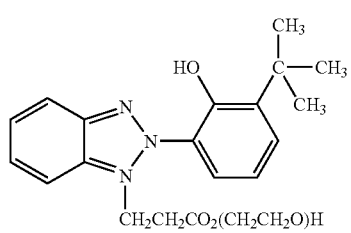

having an average molecular weight of 637, about thirty-five weight percent of poly(oxy-1,2-ethanedlyl), α-(3-(3-(2H-benzotriazol-2-yl)-5-(1,1-dimethylethyl)-4-hydroxypheny-1)-1-oxopropyl-ω-(3-(3-2H-benzotrazol-2-yl)-5-(1,1-diamethylethyl)-4-hydroxyphenyl)-1-oxopropyoxy), of the formula having an average molecular weight of 975, and the remainder (about thirteen weight percent of polyethylene glycol (300 molecular weight), which is used to functionalize the Tinuvin® 1130; Tinuvin® 292 and Tinuvin® 328, [2-(2'-hydroxyl-3, 5'-di-tert-amylphenyl)benzotri azole].

Finally, an antioxidant is employed. A preferred antioxidant is 3,5-di-tert-butyl-hydroxycinnamate, known as IRGANOX® 1076, commercially available from Ciba Geigy.

A preferred UV stabilizer/antioxidant additive composition comprises about 70-75 weight percent of Tinuvin® 1130, 10-15 weight percent IRGANOX® 1076 and 10-20 weight percent of Tinuvin(® 328.

The concentration of the additives, e.g. UV stabilizer, antioxidant, leveling agent, etc. of the total formulation will, of course, depend upon the desired use of the formulation and will be varied accordingly in a manner well known to those skilled in the art. Typically, where the reactants are HUNTSMAN D-2000 and ISONATE® 2143L or BAS7 218, the carrier solvent is acetone and the leveling agent GLYDDEX® N-10 is employed, the polyol component of the stabilizing carrier in the reaction solution is present in an amount which is in the ratio of the oligomeric diamine derivatives to the polyol of 5 to 2.66 to 1, preferably between 4.25 and 1.75 to 1, and, most preferably 4.0 to 1.

If a mixture of polyols is employed, e.g., ethylene glycol and propylene glycol, each polyol preferably should be present in equal amounts. If each polyol of the mixture of polyols is not present in equal amounts in making up the ratio of diamine to polyol, then the cure time and storage time will vary. For example, where a mixture of ethylene glycol ("EG") and propylene glycol ("PPG") is employed and the ratio of EG/ISONATE® 2143L to PPG/ISONATE® 2143L ("RATIO") is greater than 1, then the following cure times are obtained:

| RATIO | CURE TIME (25°) |
|---|---|
| 1.0 | 1.5-2 hours |
| 1.25 | 6-7 hours |
| 2.0 | 28-32 hours |

Additionally, typically, the ratio of N-10/218 is equal to or less than the ratio of EG+PPG/218. If it is greater, then the dry times of the coatings resulting from the reaction solution are lengthened. When the ratio is less than 1, the flow and spreadability of the reaction solution is reduced. The ratio range is typically 0.72 to 1.3, preferably 0.85 to 1.15, and most preferably 1.0 for N-10/218 to EG+PPG/218.

Finally, the ratio of EG+N-10/2143L to PPG+N-10/2143L is typically 1, whereby an optimum drying time of about 45 minutes to one hour and fifteen minutes at 25° C. is obtained. Ratios of less than or more than 1 typically produce reaction solutions with proportionate increases in drying times.

Another ratio which is considered is the ratio of EG/N-10 and PPG/N-10 which typically are equal to each other as well as equal to twice that of (EG+PPG)/2143L. Typically, the

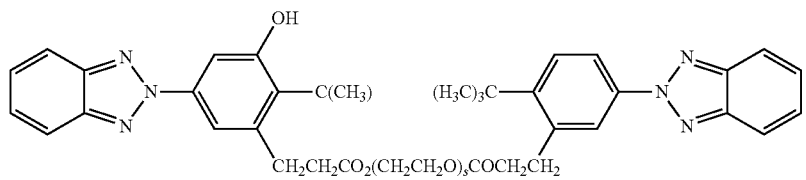

ratio of EG/N-10 to PPG/N-10 is 0.8 to 1.42, preferably 0.92 to 1.2 and most preferably 1.0.

Mechanics of Suspended Polymerization

It is hypothesized that the resultant single pot polyurea formulation having a very long shelf life without any solidification or gelling of the polyurea, e.g., 9 to 12 months at a temperature of 5 to 45° C., is due to an in situ ionic shielding action. This ionic shielding action is only a hypothesis and is not to be a limiting factor of the subject invention. The in situ ionic shielding action is hypothesized to be obtained by the reaction of the stabilizing solvent, e.g., acetone, and the polyol, e.g., a mixture of ethylene glycol and propylene glycol. This in situ reaction and its continued maintenance while in a sealed and lidded container is believed to be the electrochemical basis for being able to provide a single pot, polyurea based, elastomer polymer composition having long term shelf life, with constant clarity, fluidity and drying time factors. It is hypothesized that the reaction between the stabilizing solvent, e.g. acetone, and the polyol, e.g., a mixture of ethylene glycol and propylene glycol, produces an excess of hydrogen ions which interact with the primary amine groups of the oligomeric aromatic diamine derivative, thereby preventing reaction thereof with the polyisocyanate until a portion of the stabilizing carrier is removed, e.g., by evaporation. The basis of this belief is presented below.

If the reaction rate depends on electrophilic (i.e., electron seeking) attack on the aromatic ring, then substituents that withdraw electrons from the ring will decrease electron density in the ring—and therefore slow down the reaction. Conversely, substituents that donate electrons will speed up the reaction. This reactivity pattern is observed with all electrophilic aromatic substitution reactions.

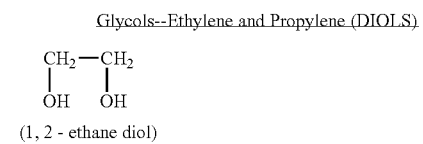

(1, 2 - ethane diol)

Alcohols are weak acids. The hydroxyl group can act as a proton donor:

Essentially, donating protons is equivalent to withdrawing electrons, corresponding to reactivity reduction.

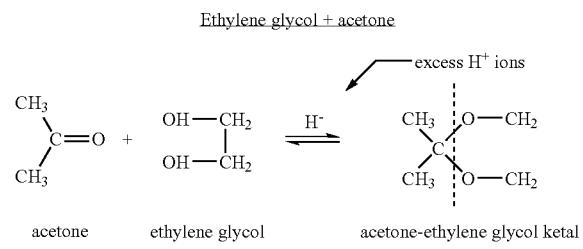

The portion of the formula to the right-hand side of the dashed line represents the elimination of the C=O double bond in the acetone molecule. Acetone-ethylene glycol ketal can be presented as a cyclic aromatic hydrocarbon.

In reactions in which a constituent is a particular solvent (primarily for viscosity purposes) substrates (solvents) that donate electrons are called donor solvents, while substrates that extract electrons are called acceptor solvents. Resonance effects being equal, the reactivity of a donor radical will always be greater with an acceptor solvent than with a donor solvent. Acetone is classified as an acceptor solvent If one applies the action of donor and acceptor solvents, one can understand the cause of the reaction between ethylene glycol:

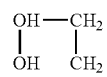

and acetone:

producing a +hydrogen ion, while at the same time eliminating the C=O double bond in acetone. It is also reasonable to assume that the constituent reactivity of ethylene glycol is considerably greater—insofar as providing +H ions in acetone, an acceptor solvent. In similar manner, the reaction of constituent propylene glycol behaves in an analogous fashion.

The reactivity of the —N=C=O— group is mainly determined by the pronounced positive (+) character of the C-atom in the cumulative double-bond sequence consisting of nitrogen, carbon, and oxygen. The positive charge at the C-atom becomes obvious if one looks at the resonance structure, which also indicates how substituents at the radical which bears the NCO group can influence this reactivity.

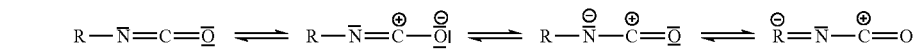

The negative charge can be delocalized, or transferred in R, if R stands for an aromatic radical.

Substituents on the aromatic ring show the known influences on the positive character of the NCO group. To wit, electron-withdrawing substituents in PARA- or ORTHO-positions increase the reactivity of the NCO-group, and electron-donating substituents lower the reactivity of the NCO group.

At this point, the following possible inhibition mechanism, or equilibrium reaction, is to be considered as a likely—and most reasonable—explanation, based on all previous stated facts.

Fact 1. The reaction of the solvent acetone with both ethylene glycol

and propylene glycol:

produces an excess of H+ ions.

Fact 2. The mobility of these reaction H+ ions is approximately 103× greater than the mobility of the NCO groups in the same common solvent-acetone.

Fact 3. The R radical of P-1000 (also P-250 and P-650) is the primary amine

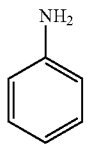

located at both ends of the oligomeric backbone diamine. See FIG. 2. Note that electrophilic substitution (and resonant replacement) is a predominant feature of reactions with benzene and delocalized π (pi) electrons on the benzene ring.

Fact 4. As discussed above, a negative charge can be delocalized or transferred in an aromatic radical. The primary amine, being an aromatic radical, bears a delocalized negative (−) change, which in terms of the order of magnitude (×3) of the glycols-acetone reaction, effectively neutralizes the negative (−) charged radicals in a manner so effective as to virtually reduce to zero the positive charge affinity of the carbon atom in the NCO group to react with the delocalized negative charge on the aromatic radical, the primary amine, principally because of the vast difference in solvent mobility. In other words, the highly mobile H+ ions literally "lock-up" the amine radicals well before the virtually immobile NCO- group molecules can find any un-neutralized negative (−) radicals.

Fact 5. When the 1-part mix is applied as a coating or sealant, e.g., over a toe nail, fingernail, or skin, the rapid evaporation of the acetone terminates the H+ ion reaction of the liquid acetone/glycols, leaving in solution primarily the oligomeric diamine/NCO reactants. In this condition—acetone removed by evaporation—the NCO/oligomeric diamine constituents experience initiation of polymerization, and continue until completely polymerized into a polyurea elastomer.

Fact 6. Hydrodynamic volume-solvent effects and molecular weight analysis: Once a polymer-solvent system has been selected, another consideration is how the polymer molecules behave in that solvent. Particularly important from the standpoint of molecular weight determinations is the resultant size, or hydrodynamic volume, of the polymer molecules in solution.

Assuming that polymer molecules of a given molecular weight are fully separated from one another by solvent, the hydrodynamic volume will depend on a variety of factors, including A) Interactions between solvent and polymer molecules;
B) chain branching;
C) conformation effects arising from the polarity and steric bulk of the substituent groups; and
D) restricted rotation caused by resonance, for example, of the type common to polyamides and polyamines:

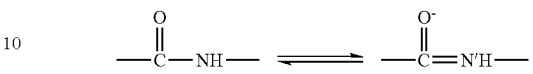

Because of Brownian motion, molecules are changing shape continuously. Therefore, any method of trying to predict molecular size (and subsequently molecular weight) must necessarily be based on statistical methods and average dimensions. If a molecule were fully extended, its size could easily be computed from knowledge of bond lengths and bond angles. Such is not the case, however, with most polymers. Because of this lack of exact knowledge of bond lengths and bond angles, size is generally expressed in terms of the following. For a linear polymer, $\bar{r}^2$=mean square average distance between chain ends. For a branched polymer, $\bar{s}^2$=square average radius of gyration about the center of gravity.

Figure 2:
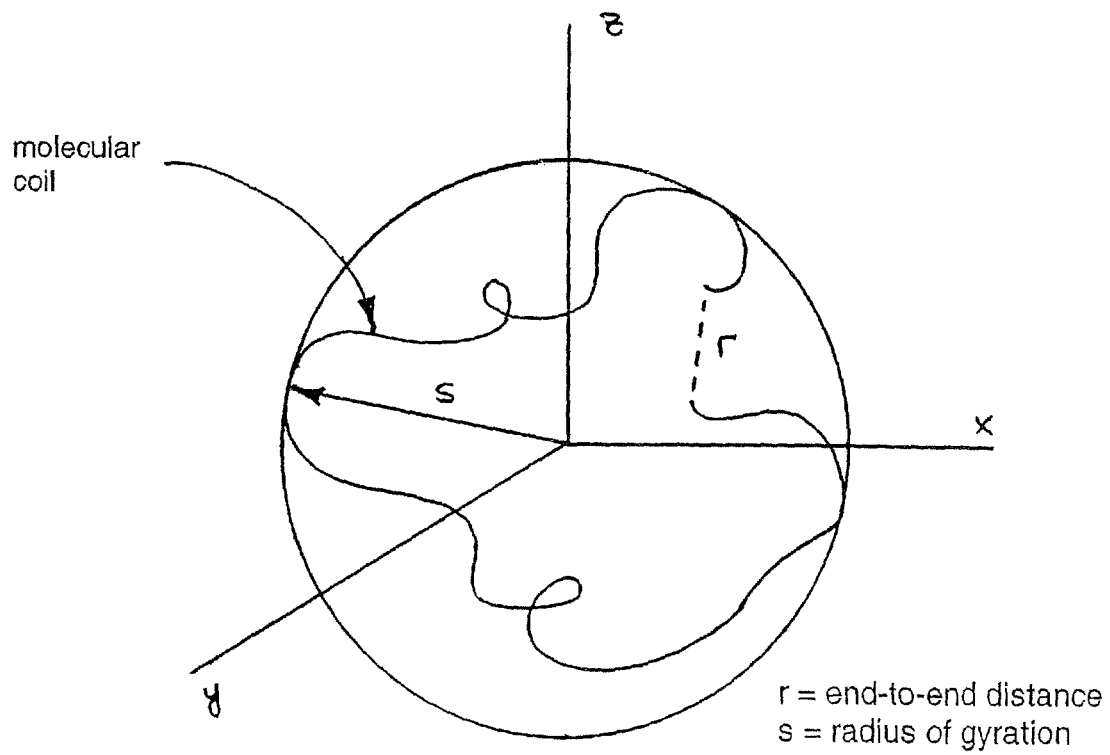
FIG. 2 is a functional block diagram depicting a polymer chain in three-dimensional space.

FIG. 2 illustrates the meaning of r and s from the perspective of a coiled structure of an individual polymer molecule having its center of gravity at the origin. The average shape of the coiled molecule is spherical. The greater the affinity of solvent for polymer, the greater the size of the sphere, or, in corollary fashion, the greater the value of s. That is, the greater the affinity of solvent for polymer, the greater the size of the sphere, i.e., the hydrodynamic volume. When solvent-polymer integration decreases, intramolecular interactions become more important, leading to hydrodynamic volume contraction.

In order to discuss the quantitative aspects of hydrodynamic volume parameters as related to solvent-polymer interaction, it is appropriate to define terms. Both r and s must be defined in terms of two factors:

A) $r_o$ and $s_o$: an unperturbed dimension; and
B) α: a volume expansion factor.

These definition permit the following relations:

$$\bar{r}^2 = r_0^2 \alpha^2$$

$$\bar{s}^2 = \bar{s}_0^2 \alpha^2$$

The unperturbed dimensions, $r_o$ and $s_o$, refer to the size of the macromolecule, exclusive of solvent effects. It is established from a combination of free rotation and intramolecular xxxx and polar interaction. The expansion factor α is defined in terms of interactions between solvent and polymer. For a linear polymer, $\bar{r}^2 = 6\bar{s}^2$. Since $$\alpha = \frac{(\bar{r}^2)^{1/2}}{(r_0^2)^{1/2}}$$

it is a conclusion that a will be >1 in a "good solvent" and the actual perturbed dimensions, r and s, will both have larger values than their corresponding "unperturbed" dimension values. The greater the value of α for a particular solvent-polymer combination, the "better" the solvent. For the special case where α=1, the polymer assumes its "unperturbed" dimensions, and behaves as an "ideal" statistical coil.

Since solubility properties vary with temperature in a given solvent, α is temperature dependent. For a specific polymer in a specific solvent, the lowest temperature at which α=1 is coiled the theta (θ) temperature, (or flory temp.) and that solvent is then called a theta solvent. Additionally the polymer is said to be in a theta state. It is usual to define the theta of a polymer as that state in which the polymer is on the brink of becoming insoluble.

The Present Invention as a Treatment Device for Onychomycosis and Urushiol-Induced Allergic Contact Dermatitis The polymer chemistry-based formulations of the present invention exhibit many properties and characteristics that make them suitable as a topically applied device for the treatment of onychomycosis and skin conditions such as urushiol-induced allergic contact. They are non-toxic; non-human carcinogenic; hydrophilic in a liquid state and hydrophobic in a cured state; and elastomeric. The formulations are non-water based; resistant to solar ultraviolet exposure degradation; and exhibit a non-degraded, long-term effective elastomeric thermal stress response over a tested range of −80 degrees F. to +225 degrees F.

The polymer chemistry-based formulations are chemically classified as a polyureathane/urea cross-linked polymer. They exhibit physical and chemical properties of a thermoset polymer; exhibit uniform structural characteristics, i.e. isotropic with uniform tensile strength and elastomeric properties in both longitudinal and radial directions; and are chemically inert to a large number of corrosive chemical agents. The formulations are biologically inert; long term (one year) immersion of wood treated with the formulations in both water and soil produced no detectable alterations in either physical or chemical properties.

A particular property of the formulations, believed to be responsible for their efficacy as topical devices for the treatment for onychomycosis and skin conditions such as urushiol-induced allergic contact dermatitis, is that when applied as a surface coating of approximately 0.003-0.007 inches thick, the formulations allow transmission of water vapor, but not water liquid. That is, thin topical coatings of the formulations are "water proof," or impervious to moisture. It is believed that this property "seals off" dermatophytes beneath a nail from, e.g., the moisture of sweat when trapped in socks and shoes, or from showers, humidity, and other environmental exposure to moisture. The elastomeric polymer device itself is nonsupportive of fungal or bacterial growth, and by preventing the absorption of environmental moisture, may preclude the growth of fungi such as dermatophytes.

Similarly, a coating of the formulations over an outbreak of urushiol-induced allergic contact dermatitis seals off urushiol-impregnated skin cells from environmental moisture, while allowing water vapor, such as perspiration, to pass. The topical device also dramatically reduces itching associated with urushiol-induced allergic contact dermatitis, although the precise mechanism of this benefit is not thoroughly understood.

In thin coatings on nails and skin, the formulations exhibit very fast drying times, and form a tough yet pliable watertight seal. The elastomeric property of the coatings prevents them from cracking and peeling as the skin (or nail) is deformed. The formulations are exceptionally amenable to blending with a large variety of organic based dyes and colorants; most notable are the colorants manufactured by HULS AMERICA, INC., known as the 844 Colorant System. Thus, in the case of treating onychomycosis, the formulations may be died and used in lieu of fingernail and toe nail paint. In the case of urushiol-induced allergic contact dermatitis, the formulations may be used without pigments, in which case they dry to a clear or translucent tone, or they may be mixed with various pigments to blend to skin tones.

Specific Formulations

The preferred elastomers for the practice of the present invention are obtained by formula ratio variations (i.e., stoichiometrically balanced) of the presently used components; these components, their chemical descriptions, and commercial product information are described below. Those of skill in the art will readily recognize that other components may advantageously be used, and the present invention is not limited to use of any of these particular components.

1) First Diamine
   a) Manufactured by Huntsman Petrochemical Corp., Houston, Tex.
   b) Chemical family. CAS #9046-10-0-Polyoxypropylenediamine
   c) Description/Use: Chemical Intermediate
   d) Chemical name: Poly[oxy(methyl-1,2-ethanediyl)], alpha-(2-aminomethylethyl)-omega-(2-aminomethylethoxy)-
   e) Commercial name: Jeffamine® D-2000

2) Second Diamine
   a) Manufactured by Arch Chemicals, Inc., Norwalk Conn.
   b) Chemical family. CAS #9046-10-0-Polyoxypropylenediamine
   c) Description/Use: Chemical Intermediate
   d) Formula: $(C_3H_6O)_n C_6H_{12}N_2O$
   e) Chemical name: Poly[oxy(methyl-1,2-ethanediyl)], alpha-(2-aminomethylethyl)-omega-(2-aminomethylethoxy)-
   f) Commercial name: POLY-A® 27-2000

3) Third Diamine
   a) Manufactured by Dorf Ketal Chemicals LLC, Stafford, Tex.
   b) Chemical family. CAS #5285-60-9 Aromatic Diamine
   c) Description/Use: Chain extender for polyurethane elastomers
   d) Chemical name: N,N'-dialkylamino-diphenylmethane; 4,4'-Bis(sec-butylamino)diphenylmethane
   e) Commercial name; Unilink 4200

4) Fourth Diamine
   a) Manufactured by Air Products and Chemicals, Inc., Allentown, Pa.
   b) Chemical family. CAS #54667-43-5 Oligomeric diamine
   c) Description/Use: Polymer-chain Extender
   d) Chemical name: Polytetramethyleneoxide-di-p-aminobenzoate;
   e) Commercial name; Versalink® P-1000

5) First Isocyanate
   a) Source: Huntsman Chemicals, Houston, Tex.
   b) Chemical family: CAS. No. 26447-40-5
   d) Description/Use: Polymer chain extension
   e) Formula description: Modified MDI
   c) Commercial name: Rubinate® 9433

6) Second Isocyanate
   a) Source: Huntsman Polyurethanes, West Deptford, N.J.
   b) Chemical family: Modified Diisocyanate
   c) Description/Use: Water-Emulsifiable MDI
   d) Formula description: Polymeric Diphenylnethane Diisocyanate and Modified MDI
   e) Commercial name: Rubinate® 9259

7) Third Isocyanate
   a) Source: Huntsman Polyurethanes, West Deptford, N.J.
   b) Chemical family: Modified Diisocyanate
   c) Description/Use: Water-Emulsifiable Crosslinker
   d) Formula description: Polymeric Diphenylmethane Diisocyanate and Modified MDI
   e) Commercial name: Rubinate® 9236
8) Fourth Isocyanate
   a) Source: Dow Chemical Company, Midland, Mich.
   b) Chemical family: Polycarbodiimide-modified Diphenylmethane Diisocyanate
   c) Description/Use: Polymer chain extension
   d) Formula description: Diphenylmethane Diisocyanate (MDI) containing Methylene Bisphenyl isocyanate, Diphenylmethane Diisocyanate (homopolymer) and Triethyl Phosphate
   e) Commercial name: Isonate® 143L Modified MDI
9) Fifth Isocyanate
   a) Source: BASF Corporation, Mount Olive, N.J.
   b) Chemical family: Aromatic isocyanate
   c) Description/Use: Polymer chain extension
   d) Formula description: Diphenylmethane-4,4'-diisocyanate (MDI), Modified MDI, and MDI Mixed Isomers
   e) Chemical name: Modified MDI
   f) Commercial name: Lupranate® 81 Isocyanate
10) Sixth Isocyanate
   a) Source: BASF Corporation, Mount Olive, N.J.
   b) Chemical family: Aromatic Isocyanate
   c) Description/Use: Polymer chain extension
   d) Formula description: 4,4'Diphenylmethane Diisocyanate (MDI), Modified MDI, and MDI Mixed Isomers
   e) Chemical name: Carbodiimide Modified MDI
   f) Commercial name: No. 218 Isocyanate
11) Seventh Isocyanate
   a) Source: Bayer Corp., Pittsburgh, Pa.
   b) Chemical family: Aliphatic Polyisocyanate
   c) Description/Use: Polymer chain extension
   d) Formula description: 1,6-Hexamethylene Diisocyanate Based Polyisocyanate
   e) Chemical name: Polymeric Hexamethylene Diisocyanate
   f) Commercial name: Desmodur® N 3200
12) Amine-Functional Resin
   a) Source: Bayer Corp, Pittsburgh, Pa.
   b) Chemical family: amine-functional reactive partner for polyisocyanates.
   c) Description/use: Crosslink with aliphatic polyisocyanate for polymer chain extension
   d) Formula: [trade secret]
   d) Commercial name: Desmophen® NH 1420
13) Modified Polyether Polyol
   a) Source: Bayer Corp, Pittsburgh, Pa.
   b) Chemical family: CAS. No. 25723-16-4-Propylene oxide adduct of trimetlhylol propane
   c) Description/use: MDI-activated thermoset—polymer converter
   d) Formula: 1,2,3-tris (hydroxymethyl) propane.
14) Ethyl Glycol. Polyol component of stabilizing carrier
   a) Available from numerous chemical distributors
   b) Chemical family: CAS #107-21-1
   c) Description/use: Solvent carrier/reactant
   d) Chemical Name: 1,2-dihydroxyethane, 1,2-ethanediol, ethane-1,2-diol
15) Propylene Glycol. Polyol component of stabilizing carrier
   a) Available from numerous chemical distributors
   b) Chemical family: CAS #57-55-6
   c) Description/use: Solvent carrier/reactant
   d) Chemical name: 1,2-propanediol; 1,2-dihdroxypropane; methyl glycol; methylethylene glycol
   e) Formula: $C_3H_8O_2$
16) Acetone, aka Propanone—Solvent Carrier/Reactant
   a) Available from numerous chemical distributors
   b) Chemical family: CAS. #67-64-1 Propanone, Acetone,
   c) Description/use: Solvent carrier/reactant
17) Acetate, aka Ethanoate,—Solvent Carrier/Reactant
   a) Available from numerous chemical distributors
   b) Chemical family: Anion of a salt or ester of acetic acid
   c) Description/use: Solvent carrier/reactant
   d) Formula: $CH_3CO_2-$
18) Mineral Spirits. Solvent Carrier/Reactant
   a) Available from numerous chemical distributors
   b) Chemical family: CAS #8052-41-3
   c) Description/use: Solvent carrier/reactant
   d) Formula: Stoddard Standard
19) Methyl Ethyl Ketone. Solvent Carrier/Reactant
   a) Available from numerous chemical distributors
   b) Chemical family: CAS #78-93-3
   c) Description/use: Solvent carrier/reactant
   d) Chemical name: Ethyl Methyl Ketone
   e) Formula: $C_4H_8O$ Formulations and Experimental Results The following representative formulations of the treatment devices of the present invention are provided. All component amounts are identified in terms of stoichiometrically balanced volume amounts expressed as milliliters.

Liquid thermosetting, hydrophobic, elastomeric, non-toxic polymer solution treatment devices were prepared by adding the reactants in the sequence given. The stoichiometrically determined volume amounts are expressed in milliliters. Solutions were stir-blended constantly at 20 paddle revolutions per minute during the sequential addition of the ingredients, and for 15-20 minutes after addition of the last ingredient. These parameters of the stir-blending process, in terms of revolutions and time, are the most optimum for obtaining maximum sequential reactivity of the ingredients during blending. The sequential mixing process was done at ambient conditions of 70-80° Fahrenheit, about 750-760 mm Hg, and relative humidity of 50-65%.

The treatment devices were applied according to the following recommended regimens. For nail fungus:

1) Cut affected nail(s) as even with tip of toe(s) or finger(s) as possible.

2) File or sand nail(s) down to at least 10-15 mils thickness (But closer to normal nail thickness should yield better effectiveness) Discard file after use and replace to avoid cross contamination of other nails and re-exposure after treatment.

3) Use nail pick or scraper to remove any dead and/or infected loose tissue from underneath the tip of the nail(s). Discard and replace after use.

4) Wash nail(s) and surrounding area with anti-bacteria soap and water, then dry thoroughly.

5) Using a Q-tip applicator, swab nail and surrounding area, with 70% Isopropyl alcohol or nail polish remover to remove excess moisture, oils, and debris that could inhibit penetration and bonding. DO NOT place applicator back into solution after contact with infected nail(s). Discard and replace applicator.

6) Apply a light topical coating of the treatment device over the prepared nail(s), the surrounding nail cuticle(s) and underneath the nail tip(s).

7) Allow to cure to a tack-free state exposed to room air. Dry-time may be accelerated by using a blow dryer on cool setting, ten minutes after application.

8) Apply next topical treatment in 24 hours, following Steps #4 thorough #7.

9) Following treatments are at 72-hour intervals.

10) Record application details, results, and condition status.

For poison ivy infections, the following regimen was observed:

1) Wash affected are with anti-bacterial soap and water, then dry.

2) Apply a light topical coating of treatment device and allow to cure to tack-free state at ambient temperature. Record any noticeable immediate reactions or changes in condition.

These treatment regimens were observed for the following formulations, with the results indicated.

| Treatment Device Formulation #1 Working Identifier: PMS-1 P-1000 | | |
|---|---|---|
| Reagent | Volume [ml] | Stoichiometric Volume Ratio |
| Acetone | 240 | 0.505 |
| Acetate | 126.75 | 0.267 |
| Versalink ® P-1000 | 55.5 | 0.117 |
| Ethyl Glycol | 7.5 | 0.016 |
| Propylene Glycol | 7.5 | 0.016 |
| Rubinate ® 9259 or 2143 | 37.5 | 0.079 |
| Total: | 474.75 | 1.000 |

Treatment 1: Poison Ivy infection covering 6 sq. in. of left arm of adult male. Itching stopped in less than a second. Condition cleared in two days. No side effects.

Treatment 2: Poison Ivy infection covering 4 sq. in. on right heel of adult male. Itching stopped in less than a second. Cool to the touch; no burning.

Treatment 3: Six-month nail fungus infection of adult male. Cleared up and has not recurred.

| Treatment Device Formulation #2 Working Identifier: PMS-3 | | |
|---|---|---|
| Reagent | Volume [ml] | Stoichiometric Volume Ratio |
| Acetone | 2888 | 0.752 |
| Acetate | 228 | 0.059 |
| Jeffamine ® D-2000 | 304 | 0.080 |

| Treatment Device Formulation #2 Working Identifier: PMS-3 | | |
|---|---|---|
| Reagent | Volume [ml] | Stoichiometric Volume Ratio |
| Unilink ® 4200 | 76 | 0.020 |
| 4012 | 144 | 0.038 |
| No. 218 Isocyanate | 198 | 0.051 |
| Total: | 3838 | 1.000 |

Treatment 1: Poison Ivy infection covering 6 sq. in. of right back of adult male. Itching stopped in less than a second. Condition cleared in two days. No sting. Cool to the touch.

Treatment 2: Twenty-five year chronic nail fungus infection in both big toes and right thumb of adult male. Thumb cleared and significant progress in both toes over 10-week treatment regimen.

| Treatment Device Formulation #3 Working Identifier: PMS-1 White | | |
|---|---|---|
| Reagent | Volume [ml] | Stoichiometric Volume Ratio |
| Acetone | 132 | 0.697 |
| Mineral Spirits | 44 | 0.232 |
| 4012 | 2.2 | 0.012 |
| Jeffamine ® D-2000 | 8.8 | 0.046 |
| No. 218 Isocyanate | 2.4 | 0.013 |
| Total: | 189.4 | 1.000 |

Treatment 1: One-year chronic nail fungus infection of left big toe of adult male. Condition 60% cleared in sixteen days, when subject ran out of treatment device. Treatment regiment resumed upon re-supply, and condition 100% cleared in two months.

Additional formulations of the medical device of the present invention are presented below.

| Formulations of Working Identifier PMS-1 | | | | | | |
|---|---|---|---|---|---|---|
| Reagent | Volume [ml] | Volume Ratio | Volume [ml] | Volume Ratio | Volume [ml] | Volume Ratio |
| Acetone | 106.8 | 0.702 | 132.0 | 0.697 | 132.0 | 0.705 |
| Mineral Spirits | 35.6 | 0.234 | 44.0 | 0.232 | 44.0 | 0.235 |
| Jeffamine ® D-2000 | 6.6 | 0.043 | 8.8 | 0.046 | 8.8 | 0.047 |
| Unilink ® 4200 | 1.2 | 0.008 | — | — | — | — |
| 4012 | — | — | 2.2 | 0.012 | — | — |
| No. 218 Isocyanate or Lupranate ® 81 Isocyanate | 2.0 | 0.013 | 2.4 | 0.013 | 2.4 | 0.013 |
| Total | 152.2 | 1.000 | 189.4 | 1.000 | 137.2 | 1.000 |

| Formulations of Working Identifier: PMS-3 | | | | |
|---|---|---|---|---|
| Reagent | Volume [ml] | Volume Ratio | Volume [ml] | Volume Ratio |
| Acetone | 650.0 | 0.776 | 850.0 | 0.782 |
| MEK | 50.0 | 0.059 | 100.0 | 0.092 |
| Jeffamine ® D-2000 | 60.0 | 0.071 | 60.0 | 0.055 |
| Unilink ® 4200 | 15.0 | 0.020 | 15.0 | 0.014 |
| 4012 | 20.0 | 0.024 | 20.0 | 0.018 |
| Ethyl Glycol | 5.0 | 0.006 | 5.0 | 0.005 |

-continued

| Formulations of Working Identifier: PMS-3 | | | | |
|---|---|---|---|---|
| Reagent | Volume [ml] | Volume Ratio | Volume [ml] | Volume Ratio |
| Propylene Glycol | 5.0 | 0.006 | 5.0 | 0.005 |
| Lupranate ®81 Isocyanate | 32.0 | 0.038 | 32.0 | 0.029 |
| Total | 837 | 1.000 | 1087 | 1.000 |

The medical device formulations of the present invention have the following physiological properties.
1. Non-Cytotoxic, MEM Elusion—MG 023-0 Dilution
2. Non-Hemolytic—In Vitro
3. Non-Pyrogenic—Test T 10, Material Mediated
4. Non-Carcinogenic—Standard Ames Salmonena Tests Although the present invention has been described herein with respect to particular features, aspects and embodiments thereof, it will be apparent that numerous variations, modifications, and other embodiments are possible within the broad scope of the present invention, and accordingly, all variations, modifications and embodiments are to be regarded as being within the scope of the invention. The present embodiments are therefore to be construed in all aspects as illustrative and not restrictive and all changes coming within the meaning and equivalency range of the appended claims are intended to be embraced therein.

What is claimed is:

1. A method of treating onychomycosis and/or urashiol-induced contact dermatitis comprising topically applying a composition comprising
    (i) a primary diamine comprising a polyether segment;
    (ii) a secondary aromatic diamine;
    (iii) a polyisocyanate; and
    (iv) optionally, a polyol,
    and/or a reaction product thereof.

2. The method of claim 1, wherein topically applying the composition comprises
    forming a solution comprising the primary diamine, the secondary aromatic diamine, the polyisocyanate, and optionally, the polyol; and/or a reaction product thereof; and
    coating an affected nail or skin with the solution.

3. The method of claim 2, wherein topically applying the composition further comprises drying the solution to form a polyurea, and/or polyureathane polymer.

4. The method of claim 3, wherein the primary diamine comprises polyoxypropylenediamine.

5. The method of claim 3, wherein the secondary aromatic diamine comprises N,N'-dialkylaminodiphenylmethane.

6. The method of claim 5, wherein the secondary aromatic diamine comprises bis(sec-butylamino)diphenylmethane.

7. The method of claim 3, wherein the polyisocyanate comprises at least one of diphenymethanediisocyanate (MDI), a polyisocyanate, MDI containing resin, aliphatic diisocyanates, aromatic diisocyanates, alicyclic diisocyanates, ethylene diisocyanate, ethylidene diisocyanate, propylene diisocyanaie, butylene diisocyanate, cyclopentylene-1,3-diisocyanate, cyclohexylene-1,4,diisocyanate, cyclohexylene-1,2-diisocyanate, 2,4-tolylene diisocyanate, 2,6-tolylene diisocyanate, 4,4'-diphenylmethane diisocyanate, 2,2-diphenylpropane-4,4'-diisocyanate, p-phenylene diisocyanate, m-phenylene diisocyanate, xylylene diisocyanate, 1,4-naphthylene diisocyanate, 1,5-naphthylene diisocyanate, diphenyl-4,4'-diisocyanate, azobenzene-4,4'diisocyanate, diphenylsulfone-4,4'diisocyanate, dichlorohexamethylene diisocyanate, tetramethylene diisocyanate, pentamethylene diisocyanate, hexamethylene diisocyanate, 1-chlorobenzene-2,4-diisocyanate, furfurylidene diisocyanate and triphenylmethane triisocyanate.

8. The method of claim 7, wherein the polyisocyanate comprises MDI, a polyisocyanate adduct and/or a MDI containing resin.

9. The method of claim 8, wherein the polyisocyanate comprises a carbodiimide modified MDI.

10. The method of claim 3, wherein the polyol comprises at least one of ethylene glycol, propylene glycol, 1,3-butylene glycol, 1,4-butylene glycol, 2,3-butylene glycol, a propylene oxide adduct of trimethylol propane, polyethylene glycol.

11. The method of claim 10, wherein the polyol comprises at least one of ethylene glycol, propylene glycol and a propylene oxide adduct of trimethylol propane.

12. The method of claim 1, wherein the composition further comprises at least one solvent selected from the group consisting of acetone, methyl ethyl ketone, methylisobutylketone, N-methylcyclohexanone, acetaldehyde, propionaldehyde, butyraldehyde, isobutyraldehyde, methyl acetate, ethyl acetate, butyl acetate, and methyl propyl acetate.

13. The method of claim 1, wherein the volume ratio of the primary diamine ranges from about 3.6% to about 12.2% v/v, based on the total volume of the composition.

14. The method of claim 1, wherein the volume ratio of the secondary aromatic diamine ranges from about 0.6% to about 6.8% v/v, based on the total volume of the composition.

15. The method of claim 1, wherein the ratio of the primary and secondary diamine to the polysicoyanate is from about 2.8:1 to about 3.8:1 by volume.

16. The method of claim 1, wherein the composition further comprises a colorant and/or pigment.

* * * * *